(12) United States Patent
Lu

(10) Patent No.: US 10,624,771 B2
(45) Date of Patent: Apr. 21, 2020

(54) STENT DELIVERY SYSTEM, CORRESPONDING FLOW DIVERSION DEVICE, AND ASSEMBLY METHOD OF FLOW DIVERSION DEVICE

(71) Applicant: AccuMedical Beijing Ltd., Beijing (CN)

(72) Inventor: Yiran Lu, Beijing (CN)

(73) Assignee: AccuMedical Beijing Ltd., Beijing (CN)

( * ) Notice: Subject to any disclaimer, the term of this patent is extended or adjusted under 35 U.S.C. 154(b) by 246 days.

(21) Appl. No.: 15/641,580

(22) Filed: Jul. 5, 2017

(65) Prior Publication Data

US 2018/0125686 A1 May 10, 2018

(30) Foreign Application Priority Data

Nov. 8, 2016 (CN) .......................... 2016 1 0979261

(51) Int. Cl.
*A61F 2/95* (2013.01)
*A61F 2/966* (2013.01)
(Continued)

(52) U.S. Cl.
CPC ................ *A61F 2/95* (2013.01); *A61F 2/958* (2013.01); *A61F 2/966* (2013.01);
(Continued)

(58) Field of Classification Search
CPC ............ A61B 17/0401; A61B 17/0467; A61B 17/0487; A61B 17/064; A61B 17/07207; A61B 1/018; A61B 2017/0034; A61B 2017/0441; A61B 2017/0464; A61B 2017/0488; A61B 2017/0649; A61F 2002/823; A61F 2002/9511; A61F 2002/9534; A61F 2002/9665; A61F 2210/0014; A61F 2230/0071; A61F 2230/0086; A61F 2240/00; A61F 2250/0098; A61F 2/95; A61F 2/958; A61F 2/966

See application file for complete search history.

(56) References Cited

U.S. PATENT DOCUMENTS

2010/0268264 A1* 10/2010 Bonnette .............. A61B 17/221
606/200

* cited by examiner

*Primary Examiner* — Ryan J. Severson
*Assistant Examiner* — Mohamed G Gabr
(74) *Attorney, Agent, or Firm* — Renner, Otto, Boisselle & Sklar, LLP

(57) ABSTRACT

A stent delivery system provided by the present application comprises: a radiopaque tip located at the distal end of the stent delivery system; a beads component comprising at least one expandable part; a funnel component comprising a distal flare structure and a proximal collapsed end, wherein the cross-section of the flare structure gradually increases from its minimum diameter to its maximum diameter along the proximal-to-distal direction; and a core wire located at the proximal end of the stent delivery system; and wherein the distal end of the beads component is fixed on the radiopaque tip and the proximal end of the beads component is fixed on the core wire; wherein the funnel component is coupled with the beads component and the core wire, and is fixed on the core wire through the collapsed end. The present application also provides a flow diversion device and an assembly method of the flow diversion device.

24 Claims, 5 Drawing Sheets

(51) Int. Cl.
  *A61F 2/958* (2013.01)
  *B29C 65/48* (2006.01)
  *A61F 2/82* (2013.01)
  *B29L 31/00* (2006.01)
(52) U.S. Cl.
  CPC ...... *B29C 65/4835* (2013.01); *B29C 65/4845* (2013.01); *A61F 2002/823* (2013.01); *A61F 2002/9511* (2013.01); *A61F 2002/9534* (2013.01); *A61F 2002/9665* (2013.01); *A61F 2210/0014* (2013.01); *A61F 2230/0071* (2013.01); *A61F 2230/0086* (2013.01); *A61F 2240/00* (2013.01); *A61F 2250/0098* (2013.01); *B29L 2031/753* (2013.01)

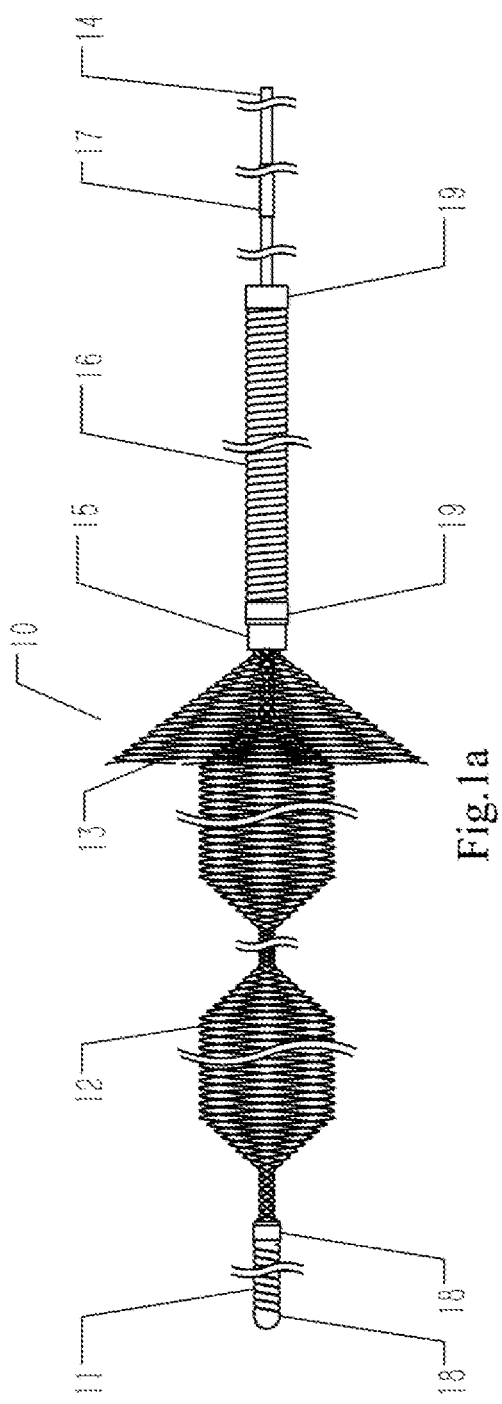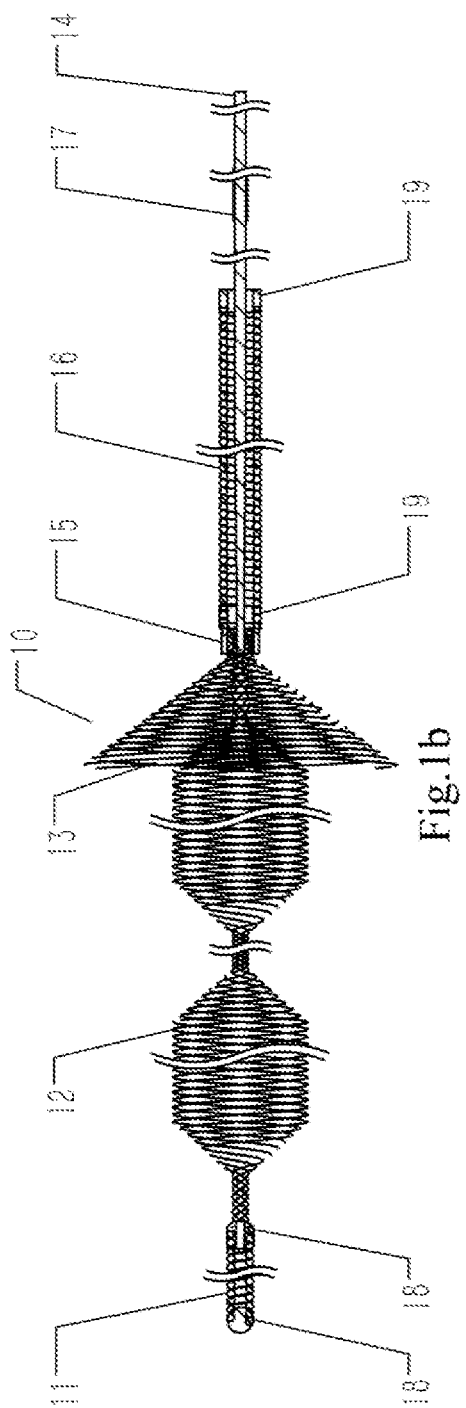

STENT DELIVERY SYSTEM, CORRESPONDING FLOW DIVERSION DEVICE, AND ASSEMBLY METHOD OF FLOW DIVERSION DEVICE

CROSS REFERENCE TO RELATED APPLICATIONS

This application claims priority to Chinese Patent Application No. 201610979261.1 filed on Nov. 8, 2016, the entire content of which is incorporated herein by reference.

FIELD OF THE INVENTION

The present application relates to the field of intervention therapy, and more specifically, to a stent delivery system as well as a corresponding flow diversion device and an assembly method of flow diversion device.

BACKGROUND OF THE INVENTION

A vascular aneurysm is a result of lesion or injury in the arterial wall, which forms a localized or diffuse dilatation or bulge on the arterial wall and mainly shows as an expansile and pulsatile tumor. Aneurysms may occur in any blood vessel and include abdominal aortic aneurysm, cerebral aneurysm, peripheral aneurysm, visceral aneurysm, etc. The wall of an aneurysm is thin and fragile, making it prone to rupturing.

Besides conventional conservative or surgical treatments, the interventional treatment is currently an important therapy for aneurysm. In the interventional treatment, it is a widely-used approach to place embolic materials such as detachable balloons, coils, etc. into the body of an aneurysm by using a catheter so that the speed of blood flow in the body of the aneurysm may be significantly reduced or even stopped. By this means, a thrombus may be gradually formed to embolize the body of the aneurysm in order to prevent the aneurysm from rupturing.

However, at least the following defects exist when the interventional embolization treatment mentioned above is adopted for large (maximum diameter of more than 10 mm) or huge (maximum diameter of more than 25 mm) aneurysms. First, it is required to use embolic materials such as coils to densely fill the aneurysm. However, large or huge aneurysms are often wide-necked aneurysms. In such cases, coils as the embolus are very easy to project out into the parent artery carrying the aneurysms, which may cause stenosis or even occlusion to the parent artery. Taking the cerebral aneurysm as an example, this may lead to serious consequences such as cerebral ischemia or even cerebral infarction. Second, the mass effect is common to large or huge aneurysms. The aneurysms may become larger, thereby compressing surrounding viscera and tissues and affecting their physiological functions. Although filling an aneurysm with coils may embolize the aneurysm, it cannot eliminate the mass effect caused by the aneurysm or may even worsen the mass effect.

One type of flow diversion device that is based on a densely-netted vascular stent (only simply called "stent") came out in recent years. This type of flow diversion device may effectively overcome the above-described defects of coil embolization in treating large or huge aneurysms. After implanted to the parent artery, the flow diversion device may interrupt blood flow from the parent artery to the aneurysm by the fine mesh of the stent and cause blood in the aneurysm to clot so as to form a thrombus, thereby occluding completely the aneurysm. In addition, the flow diversion device may be provided for vascular endothelial cells to climb thereon. After the flow diversion device is covered by vascular endothelial cells, a permanent biological sealing may be formed on the neck of the aneurysm, which may help the parent artery to recover and become a normal vessel.

However, there are still defects in the stent-based flow diversion device as described above. Taking the Pipeline™ embolization device of Medtronic PLC as an example, the stent is configured as being rotatable around the core component of the flow diversion device. Accordingly, torsional stress may be generated between the stent and the core component (e.g. the core wire) while the stent is pushed to the lesion through circuitous and curved vessels. As a consequence, when the compressed stent arrives at the lesion, it may not be able to deploy automatically due to the effect of the torsional stress. Since the torsional stress may be unpredictable, failure in deploying the stent might still exist even if the deploying is manually done by twisting the core wire.

In addition, sharpness of a radiographic image may be limited for vessels of small diameters, which in turn may influence precision in the position where a stent is placed. In the case of the Pipeline embolization device, it would be very difficult to pull the deployed stent back to the catheter and re-adjust the placement position when the deployed stent is found at an unsatisfactory position.

After problems like a failure in deploying the stent or an unsatisfactory placement position of the stent occur, it may need to take the entire Pipeline embolization device out, which may not only cause the expensive device out of use but also cause injury to the patient due to the larger diameter of a deployed stent.

SUMMARY OF THE INVENTION

The technical solution to be solved by the present application is to provide a stent delivery system, a corresponding flow diversion device, and an assembly method of the flow diversion device. The flow diversion device may be used for treatment of aneurysms and have the advantage of easy deployment and retrieval of the stent.

To solve the above technical problem, a stent delivery system is provided by the present application, said stent delivery system comprises: a radiopaque tip located at the distal end of the stent delivery system; a beads component comprising at least one expandable part; a funnel component comprising a distal flare structure and a proximal collapsed end, wherein the cross-section of the flare structure gradually increases from its minimum diameter to its maximum diameter along the proximal-to-distal direction; and a core wire located at the proximal end of the stent delivery system; and wherein the distal end of the beads component is fixed on the radiopaque tip and the proximal end of the beads component is fixed on the core wire; wherein the funnel component is coupled with the beads component and the core wire, and is fixed on the core wire through the collapsed end.

Preferably, the beads component comprises a plurality of expandable parts and a plurality of non-expandable parts arranged alternatively along the axial direction, or, preferably, the beads component comprises a plurality of expandable parts continuously arranged continuously along the axial direction and two non-expandable parts located at the two ends. Or, preferably, the beads component comprises a coil, said coil comprising at least two portions in different diameters.

Preferably, a proximal coil is coupled to the outermost part of the distal end of the core wire, and the proximal coil is fixed on the core wire. More preferably, a marker band is also coupled to the outermost part of the distal end of the core wire, said marker band being located at the distal end of the proximal coil and being fixed on the proximal coil.

Preferably, a heat-shrink tube is coupled to the proximal end of the core wire.

Preferably, the plurality of expandable parts are in at least one of a bipyramid shape, a spherical shape, a flat-spherical shape, or a long-spherical shape.

Preferably, the beads component and the funnel component are made of super-elastic materials, shape memory materials, or piezoelectric materials.

Preferably, the beads component and the funnel component are made through a fine wire braiding technique.

Preferably, the beads component is braided with six to sixty-four fine wires, and the funnel component is braided with four to twenty-four fine wires. More preferably, the braided density of the beads component is between 20 PPI and 250 PPI.

Preferably, the radiopaque tip, the beads component, the funnel component, the core wire, the marker band, and the proximal coil are fixed through gluing. More preferably, the radiopaque tip and the beads component are glued by ultraviolet (UV)-curing adhesives. Or, more preferably, the beads component, the funnel component, the core wire, the marker band, and the proximal coil are glued by heat-curing epoxy adhesives.

Preferably, a covering part is provided on the distal radiopaque tip to confine all distal open ends of the beads component within the covering part.

A flow diversion device is also provided by the present application, said flow diversion device comprises a stent, a stent delivery system, and an introducer tube, wherein the stent and the stent delivery system are confined in the lumen of the introducer tube under an initial state. The stent delivery system comprises: a radiopaque tip located at the distal end of the stent delivery system; a beads component comprising at least one expandable part; a funnel component comprising a distal flare structure and a proximal collapsed end, wherein the cross-section of the flare structure gradually increases from its minimum diameter to its maximum diameter along the proximal-to-distal direction; and a core wire located at the proximal end of the stent delivery system. The distal end of the beads component is fixed on the radiopaque tip and the proximal end of the beads component is fixed on the core wire; and wherein the funnel component is coupled with the beads component and the core wire, and is fixed on the core wire through the collapsed end; and wherein, under the initial state, the stent is located outside the beads component, and the flare structure of the funnel component covers at least a proximal part of the stent.

Preferably, the number and maximum diameter of the at least one expandable part are determined respectively according to the length and diameter of the stent.

Preferably, compared with the length and the maximum diameter under a fully deployed state, the length is shorter and the maximum diameter is smaller under the initial state for each expandable part.

Preferably, under a fully deployed state, the maximum diameter of the flare structure of the funnel component is larger than the maximum diameter at the proximal end of the stent.

Preferably, a proximal coil is couple to the outermost part of the distal end of the core wire, and the proximal coil is fixed on the core wire. More preferably, a marker band is also couple to the outermost part of the distal end of the core wire, said marker band being located at the distal end of the proximal coil and being fixed on the proximal coil.

Preferably, a heat-shrink tube is coupled to the proximal end of the core wire.

An assembly method of a flow diversion device is also provided by the present application, said assembly method comprises: coupling a core wire, a beads component, a funnel component sequentially from inside to outside, and fixing the proximal end of the beads component and the collapsed end of the funnel component onto the distal end of the core wire; coupling a marker band to the outer part of the core wire, the beads component, and the funnel component, and fixing a proximal coil onto the distal end of the core wire, wherein the marker band is fixed onto to the distal end of the proximal coil; fixing the distal end of the beads component onto a radiopaque tip, thereby completing the assembly of the stent delivery sub-assembly; inserting the stent delivery sub-assembly into a stent; compressing and inserting the combined stent and stent delivery sub-assembly into an introducer tube.

Preferably, the fixings between the core wire, the beads component, the funnel component, the marker band, and the proximal coil are implemented by gluing with heat-curing epoxy adhesives at key points.

Preferably, the fixing between the beads component and the radiopaque tip is implemented by gluing with ultraviolet (UV)-curing adhesives at key points.

Preferably, the assembly method further comprises coupling the heat-shrink tube to the proximal end of the core wire Preferably, the assembly method further comprises sterilizing the assembled flow diversion device.

The devices described above can be used for aneurysm treatment, wherein the stent is easily released and may be retrieved. Said devices may reduce risks in interventional surgeries, as well as rejection rate of expensive medical equipments, thereby improving the success rate and economy of interventional treatment for aneurysms. Moreover, the devices described above are suitable for stents of varied designs and materials and do not rely on any particular design and manufacturing process of the stent, thereby also improving versatility of the devices.

BRIEF DESCRIPTION OF DRAWINGS

The aforementioned features and other features of the application will be further described in the following paragraphs by referring to the accompanying drawings and the appended claims. It will be understood that, the accompanying drawings merely illustrate certain embodiments in accordance with the present application and should not be considered as limitation to the scope of the present application. Unless otherwise specified, the accompanying drawings need not be proportional, and similar reference characters generally denote similar elements.

FIGS. 1a-1b illustrate schematic diagrams of a stent delivery system according to an embodiment of the present application.

DETAILED DESCRIPTION OF THE EMBODIMENTS

Figure 2A:
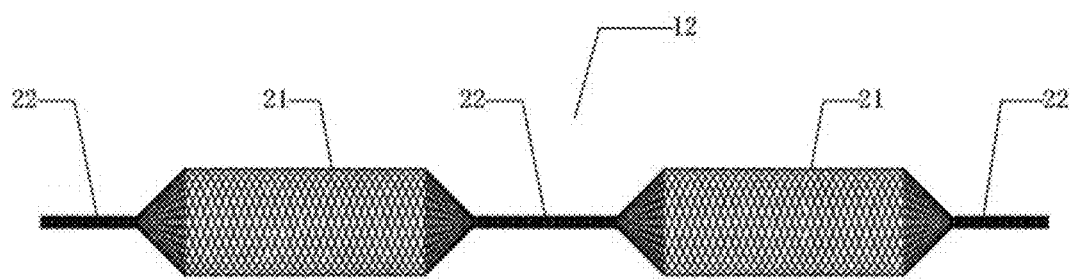
FIGS. 2a-2b illustrate schematic diagrams of a beads component according to the above embodiment in FIGS. 1a-1b.

The following detailed description refers to the accompanying drawings as a part of the present application. The illustrative embodiments described in the detailed description, the accompanying drawings and the claims are not limiting, and other embodiments may be adopted, or modifications may be made without deviating from the spirit and subject of the application. It would be appreciated that the various aspects of the application described and graphically presented herein may be arranged, replaced, combined, divided and designed in many different configurations, and these different configurations are implicitly comprised in the application.

FIGS. 1a-1b illustrate schematic diagrams of a stent delivery system 10 according to an embodiment of the present application, which may be used to deliver vascular stents having a large metallic surface area and a low void ratio such as the densely-netted stent mentioned above to the target position (e.g. an opened aneurysm). FIG. 1a is a side view and FIG. 1b is a cross-sectional view. As shown, the stent delivery system 10 consists of a number of components, including a radiopaque tip 11, a beads component 12, a funnel component 13, and a core wire 14. Furthermore, the stent delivery system 10 may also include a marker band 15, a proximal coil 16, and a heat-shrink tube 17, as well as gluing points 18 on both ends of the radiopaque tip 11 and gluing points 19 on both ends of the proximal coil 16. These components of the stent delivery system 10 are described in details as below.

The radiopaque tip 11 is located at the distal end of the stent delivery system 10 to ensure that the distal end of the entire stent delivery system 10 is visible under a fluoroscopic equipment, thereby facilitating identifying its position and direction of movement relative to surrounding vessels during the interventional surgery. As shown, in one embodiment, the distal radiopaque tip 11 may be in a coil-like shape and may be made of platinum, platinum alloy (e.g. 92% platinum and 8% tungsten), tantalum, radiopaque polymer materials, etc.

Moreover, since the beads component 12 is preferably made of metal wires or coils, the distal radiopaque tip 11 is also used to capture and fix all open ends at the distal end of the beads component 12, so as to prevent unclosed metal wires or coils from injuring blood vessels or damaging the stent during the delivering process. Specifically, in one embodiment, as shown by the gluing point 18 at the proximal end of the distal radiopaque tip 11 in FIG. 1a, the two components may be fixed through gluing with ultraviolet (UV)-curing adhesives, epoxy, or other polymeric adhesives or through soldering with solders. In addition, in this embodiment, the distal end of the distal radiopaque tip 11 may similarly have a gluing point 18 to cover any sharp edge that may exist on the coil of the radiopaque tip so as to avoid or minimize its damages to blood vessels. In another embodiment, a covering part may be provided onto the distal radiopaque tip 11 so that all open ends at the distal end of the beads component 12 may be confined within the covering part. It would be appreciated by those skilled in the art that the distal radiopaque tip 11 may be designed in various shapes or lengths, which are not limited by the present application.

Generally, the core wire 14 of the stent delivery system 10 is designed to have a diameter that gradually decreases from the proximal end to the distal end and a cone-shaped tip, which may allow the core wire 14 to have enough flexibility, so that the delivery system 10 and the stent can move flexibly in curved vessels and be guided to the lesion. The core wire 14 as a whole may be made of metals, polymers, alloys, hyper-elastic materials, or shape memory materials known in the art. Alternatively, the core wire may also be made of two or more materials. Core wires may have a number of selectable diameters, e.g. the maximum diameter at the distal end varies from 0.0127 mm (0.0005") to 0.97 mm (0.038"), and selectable lengths, e.g. it varies from 30 cm to 300 cm.

Furthermore, the stent delivery system 10 may also include a heat-shrink tube 17 located outside the core wire 14. The heat-shrink tube 17 is located at the proximal end of the core wire 14 and is always kept outside the body of the patient during the interventional surgery so as to indicate a relative position of the entire delivery system within the body of the patient. In one preferable embodiment, the heat-shrink tube 17 is made of PET or PEBAX.

As described above, the distal end of the beads component 12 is fixed on the distal radiopaque tip 11. Meanwhile, the proximal end of the beads component 12 is fixed on the distal end of the core wire 14. Similarly, the beads component 12 and the core wire 14 may be fixed by gluing. In the embodiment shown in FIGS. 1a-1b, a marker band 15 and a proximal coil 16 are coupled in sequence at the outermost part of the distal end of the core wire 14. In this embodiment, the marker band 15 is in a cylindrical shape and may be made of platinum alloy (e.g. 90% platinum and 10% iridium) or other radiopaque materials, so as to facilitate identifying the position of the proximal end of the stent delivery system 10 during the interventional surgery. In this embodiment, the proximal coil 16 may be of stainless steel or other alloy materials. As the tip of the core wire 14 is cone-shaped and has a fine diameter, coupling the proximal coil 16 may prevent the cone-shaped tip from bending during the delivering process so as to ensure elasticity and flexibility of the core wire 14. In one embodiment, the length of the proximal coil 16 may be substantially a quarter of the length of the entire core wire 14. In addition, in one embodiment, as shown by the gluing points 19 in FIGS. 1a-1b, the proximal coil 16 may be fixed on the core wire 14 and glued to the marker band 15 by using materials such as heat-curing epoxy adhesives. In another embodiment, the proximal coil 16, the marker band 15, and the core wire 14 may be fixed through soldering. In another embodiment, the marker band 15 may project out of the distal end of the core wire 14, and the beads component 12 may be inserted from the middle (i.e. core) such that the distal end of the core wire 14 may reach the middle of the beads component 12 as well as the middle of the stent. In this embodiment, the distal end of the core wire 14 has a marker structure. Thus, the marker structure at the distal end of the core wire 14 may always identify relative positions of the stent to the catheter when the stent is deployed during surgery.

Figure 5A:
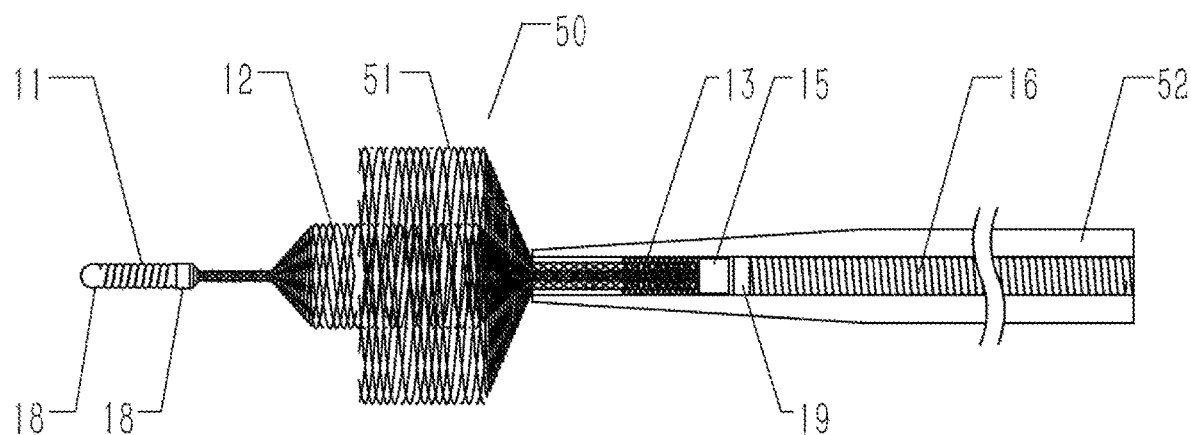
FIGS. 5a-5c illustrate schematic diagrams of a flow diversion device according to an embodiment of the present application.

The beads component 12 is designed to be placed within the stent (e.g. the stent 51 in FIG. 5a). During the process of interventional treatment, the beads component 12 may achieve the following effects: 1) once arriving at the target position, by pushing the core wire 14 towards the distal direction, the beads component 12 and the stent are pushed out of the catheter (not shown) together, and the stent is pushed to expand by the expansion of the expandable parts of the beads component 12 so that the stent may be fully deployed at the target position and thereby contact the vessel wall at the treatment position; 2) when the initial deploying position for the stent is not satisfying, by pulling the core wire 14 back towards the proximal end, the beads component 12 and the stent are pulled back to the catheter (not shown) and return to the compressed state so that the deploying position for the stent may be re-adjusted or, if necessary, the stent and its delivery system 10 may be taken out from the patient.

Figure 2B:
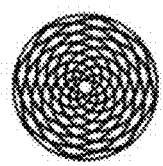

FIGS. 2a-2b illustrate schematic diagrams of the beads component 12 according to the above-described embodiment. In order to achieve the above effects, the beads component 12 is designed to have a substantially circular cross section (as shown in FIG. 2b) and varied cross-sectional diameters along its effective length. In the embodiment shown in FIGS. 2a-2b, the beads component 12 is designed to have multiple (e.g. two) bead-shaped expandable parts 21 and multiple (e.g. three) non-expandable parts 22 which are arranged in an alternate structure. The multiple expandable parts 21 and non-expandable parts 22 are one continuous piece and may be made of Nitinol alloy or other alternative super-elastic materials, shape memory materials, or piezoelectric materials such as metals, alloys, polymers, etc. In one embodiment, the beads component 12 may be braided with multiple (e.g. six to sixty-four) Nitinol alloy wires, of which the braided density (weft density) may be correspondingly from approximately 20 PPI (picks per inch) to 250 PPI so as to match the braided density of the stent. In one preferred embodiment, the beads component 12 may be braided with 24 Nitinol alloy wires to have a braided density of approximately 65 PPI. Accordingly, in this preferred embodiment, in a fully deployed state, the length of each expandable part 21 is approximately 5 mm and the maximum diameter is approximately 2 mm so as to match (e.g. equal to, slightly smaller than, or smaller than) the inner diameter of the stent. Accordingly, also in this preferred embodiment, in the fully deployed state, the length of each non-expandable part 22 located in the middle of the beads component 12 is approximately 5 mm, and the length of each non-expandable part 22 located at the two ends of the beads component 12 is at least 6 mm. It would be appreciated by those skilled in the art that the expandable part 21 and the non-expandable 22 may also be designed to have other suitable sizes. In addition, it would also be appreciated by those skilled in the art that the number of expandable parts 21 on the beads component 12 may be determined based on the length of the stent so that the effective length of the beads component 12 may be matched with the length of the stent. In one preferred embodiment, the number of the expandable parts 21, the non-expandable parts 22 or a combination of the two parts may vary from 1 to 40.

The minimum cross-sectional diameter of the beads component 12 may be determined through various ways. In the embodiment shown in FIGS. 2a-2b, the diameter of the open end at the proximal end of the beads component 12 (i.e. the diameter of the non-expandable part 22 at the proximal end) may be designed according to the inner diameter of the cylindrical marker band 15, so that the open end of the beads component 12 can appropriately pass through the marker band 15 and then be coupled to the core wire 14. Similarly, the diameter of the open end at the distal end of the beads component 12 (i.e. the diameter of the non-expandable part 22 at the distal end) may be substantially equal to the diameter at the proximal end of the distal radiopaque tip 11 so as to fix the two. For the purpose of easy manufacturing, in the embodiment shown in FIGS. 2a-2b, the diameters of the connection ends of the expandable parts 21 and non-expandable parts 22 within the beads component 12 may also be substantially equal to the inner diameter of the marker band 15. However, the present application does not limit the designs of the beads component 12 to the embodiments described above. It would be appreciated by those skilled in the art that diameter of the non-expandable part may be flexibly determined according to the material, size, and manufacturing processing of the beads component as well as the shape of the expandable part.

Now turning to FIGS. 3a-3d, illustrated are schematic cross-sectional views of various alternative designs 12a-12d of the beads component according to embodiments of the present application. It would be appreciated by those skilled in the art that these alternative designs are only for illustration but not to limit the scope of the present application.

Figure 3A:
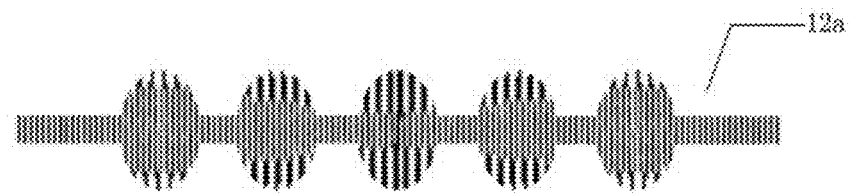
FIGS. 3a-3d illustrate schematic cross-sectional views of various alternative designs of the beads component according to embodiments of the present application.
Figure 3B:
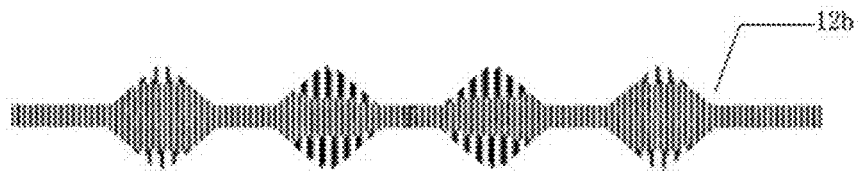

In FIGS. 3a and 3b, the beads components 12a and 12b are respectively designed to have expandable parts in a flat-spherical shape and a bipyramid shape, so that they may have varied cross-sectional diameters along their effective lengths. The non-expandable parts and other designs of the beads components 12a and 12b are similar to those of the beads component 12, which will not be deliberated again.

Figure 3C:
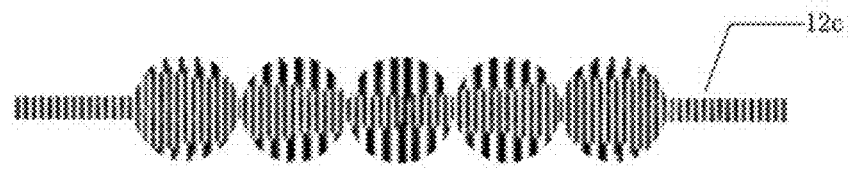

FIG. 3c illustrates an exemplary design 12c of the beads component, which has a spherical-shaped expandable part. Different from the designs in FIGS. 2a-2b and FIGS. 3a-3b, there is no corresponding non-expandable part between expandable parts in beads component 12c, that is, the beads component is directly formed by successively arranging multiple expandable parts and only having the non-expandable parts at the two ends of the component to connect other components of the stent delivery system. Manufacturing materials and process of the beads component 12c are similar to those of the beads component 12, which will not be deliberated again.

Figure 3D:

FIG. 3d illustrates an exemplary design 12d of the beads component. Different from the manufacturing process for beads components 12 and 12a-12c, the beads component 12d is designed to be made of an elastic coil and have at least two different diameters alternately configured along its effective length. According to the above description of the beads component 12, it would be appreciated by those skilled in the art that the maximum diameter of the coil forming the beads component 12d may be designed to match the inner diameter of the stent.

Various exemplary implementations of the beads component in the stent delivery system have been described in connection with FIGS. 2a-2b and FIGS. 3a-3d. It would be appreciated by those skilled in the art that expandable parts in other shapes or a combination of expandable parts and non-expandable parts in different shapes may be used to form the beads component according to the present application, and these potential designs that may facilitate opening of the stent also fall into the scope of the present application.

Figure 4A:
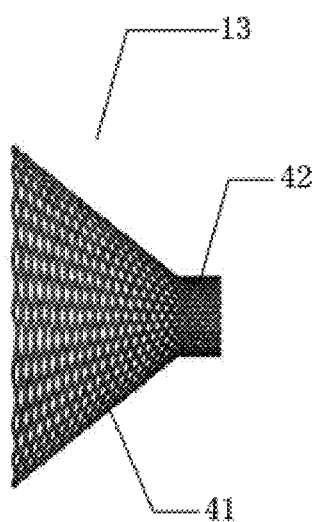
FIGS. 4a-4b illustrate schematic diagrams of a funnel component according to an embodiment of the present application.
Figure 4B:
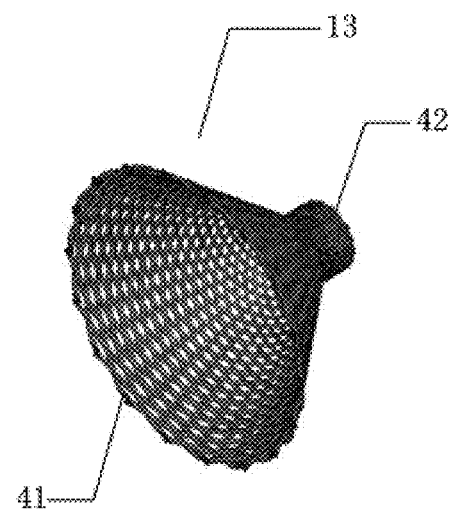

FIGS. 4a-4b illustrate schematic diagrams of the funnel component 13 in the stent delivery system according to an embodiment of the present application, where FIG. 4a is a side view and FIG. 4b is a perspective view. Similar to the beads component 12, the funnel component 13 may also be made of Nitinol or other super-elastic, shape memory, or piezoelectric materials such as metals, alloys, or polymers, and may be made through fine wire braiding. As shown, a flare structure 41 is formed at the distal end of the funnel component 13. The flare structure is designed to have a substantially circular cross-section, which gradually increases from its minimum diameter to its maximum diameter along the proximal-to-distal direction. In one embodiment, the maximum diameter is designed to be larger (e.g. slightly larger) than the maximum diameter at the proximal end of the stent in a fully deployed state so as to completely cover the proximal end of the stent. A collapsed end 42 is formed at the proximal end of the funnel component 13. The collapsed end 42 is designed to have a cylindrical shape and couple to the open end at the proximal end of the beads component 12 and core wire 14 sequentially from outside to inside. The diameter of the collapsed end 42 may be designed according to the inner diameter of the marker band 15, so as to allow the collapsed end 42 to appropriately pass through the marker band 15 and couple to the beads component 12 and the core wire 14.

In one embodiment, the funnel component 13 may be made by braiding multiple (e.g. four to twenty-four) Nitinol alloy wires, the length of the distal flare structure may vary from 2 mm to 10 mm and at least partially overlap with the stent in the axial direction. Alternatively, the distal flare structure may be designed to cover a part or the entire length of the stent in the compressed state. In one preferred embodiment, the funnel component 13 is braided by using sixteen Nitinol alloy wires. Accordingly, in this preferred embodiment, the length of the distal flare structure of the funnel component 13 is approximately 5 mm and the maximum diameter of the flare is approximately 6 mm. It would be appreciated by those skilled in the art that the funnel component 13 may have other appropriate sizes. In another preferred embodiment, the funnel component 13 is made by braiding fine wires. The fine wires may be bended and the bended parts may be used as the flare structure 41, so that there is no sharp tip at the open end and all opening tips are bound at one side of the collapsed end 42 to avoid or minimize damages to blood vessels.

The funnel component 13 and the beads component 12 together may facilitate a full deployment and retrieval operation of the stent. Functions of the funnel components 13 and the beads component 12 in the operations of deploying and retrieving the stent will be described below in connection with other figures.

Figure 5B:
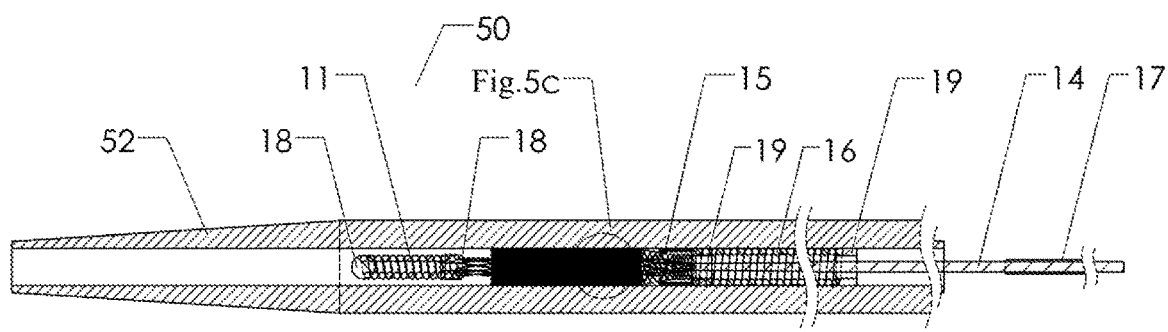
Figure 5C:
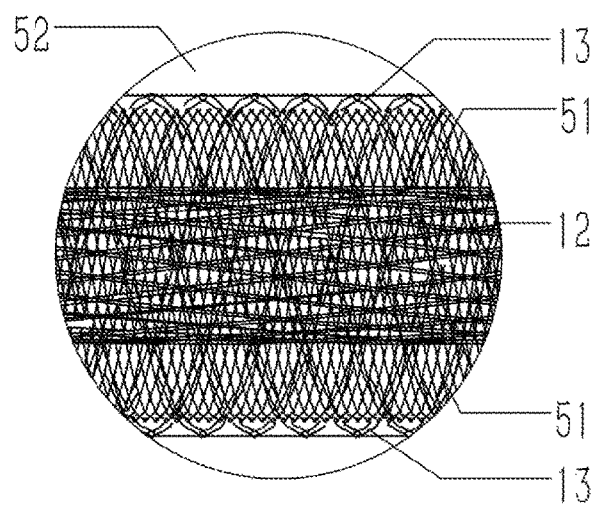

FIGS. 5a-5c illustrate schematic diagrams of a flow diversion device 50 according an embodiment of the present application, where FIG. 5a illustrates the device in a partially deployed state, FIG. 5b illustrates the device in a compressed state, and FIG. 5c is an enlarged partial view of FIG. 5b. As shown, the flow diversion device 50 is obtained based on the stent delivery system 10. More specifically, besides the distal radiopaque tip 11, the beads component 12, the funnel component 13, the core wire 14 (not shown in FIG. 5a), the proximal marker band 15, the proximal coil 16, the heat-shrink tube 17 (not shown in FIG. 5a), the gluing points 18 on both ends of the distal radiopaque tip 11 and the gluing points 19 on both ends of the proximal coil 16 that form the stent delivery system 10, the flow diversion device 50 also comprises a stent 51 and an introducer tube 52.

The stent 51 is placed outside the beads component 12. In a fully deployed state, the length of the stent may be substantially equal to or slightly smaller than the length of the beads component 12. The stent 51 may be manufactured by any known techniques such as braiding, coating, laser cutting, etc. and be made of any known materials such as metal, alloy, polymer, etc., which are not limited by the present application. It would be appreciated by those skilled in the art that the diameter and length of the stent 51 depend on conditions of the treatment position in the blood vessel. In one embodiment, the diameter of the stent 51 may be approximately between 2 mm and 10 mm, and the length may be approximately between 5 mm and 100 mm.

The flow diversion device 50 shown in FIG. 5a is in a partially deployed state. Under this state, a portion of the beads component 12 and the stent 51 has been pushed out of the introducer tube 52. The stent 51 may be expanded due to its elasticity and the radial tension of the beads component 12 so that the stent 51 may touch the vessel wall at the treatment position. Then, further advancement of the core wire 14 may fully deploy the stent in the vessel. Then, by retracting the core wire 14 towards the proximal end, the stent delivery system 10 may be pulled back to the introducer tube 52 and delivery of the stent may be completed.

Accordingly, based on the structural design of the beads component 12 and the funnel component 13, the flow diversion device 50 may be retrieved back into the catheter before the stent 51 is fully deployed.

The flow diversion device 50 shown in FIG. 5b is in a compressed state. Under this state, all components of the flow diversion device 50 are confined within the lumen of the introducer tube 52 so that the entire flow diversion device 50 is in a compressed state (also known as the initial state).

Under this state, the beads component 12 may compress due to the radial pressure so that its diameter and length in this state are smaller than those in the deployed state. Meanwhile, the radial tension generated by the compressed beads component 12 may provide friction that may make the stent 51 move, along its axis, towards the distal end for delivery or towards the proximal end for retrieval. As the beads component 12 has tapered diameters on its expandable parts, it may be easily pulled back into the catheter during the retrieving process.

Meanwhile, under this state, the distal flare structure of the funnel component 13 may also compress under the radial pressure. As the flare structure at least partially overlaps with the stent 51 along its axis, a part of the flare structure covering the proximal end of the stent 51 may generate radial pressure to the stent 51 and, thereby, provide friction that may make the stent 51 move along its axis for delivery or retrieve. In addition, as the funnel component 13 may effectively cover the proximal end of the stent 51, it may prevent the proximal end of the stent 51 from being bended by the introducer tube 52 during the process of retrieving the stent 51 back into the introducer tube 52, thereby allowing re-introduction of the device into the catheter.

FIG. 5c is an enlarged partial view of FIG. 5b, which illustrates relative positions of the beads component 12, the stent 51, and the funnel component 13 under the compressed state in the introducer tube 52.

The introducer tube 52 may be used to maintain the flow diversion device 50 and the stent 51 in the initial compressed state. At the beginning of the interventional surgery, the introducer tube 52 is plugged into the head of the catheter. Both ends of the introducer tube 52 may be tapered and smooth, and the introducer tube 52 may be made of materials known in the art such as high density polyethylene (HDPE), which are not limited by the present application.

Figure 6:
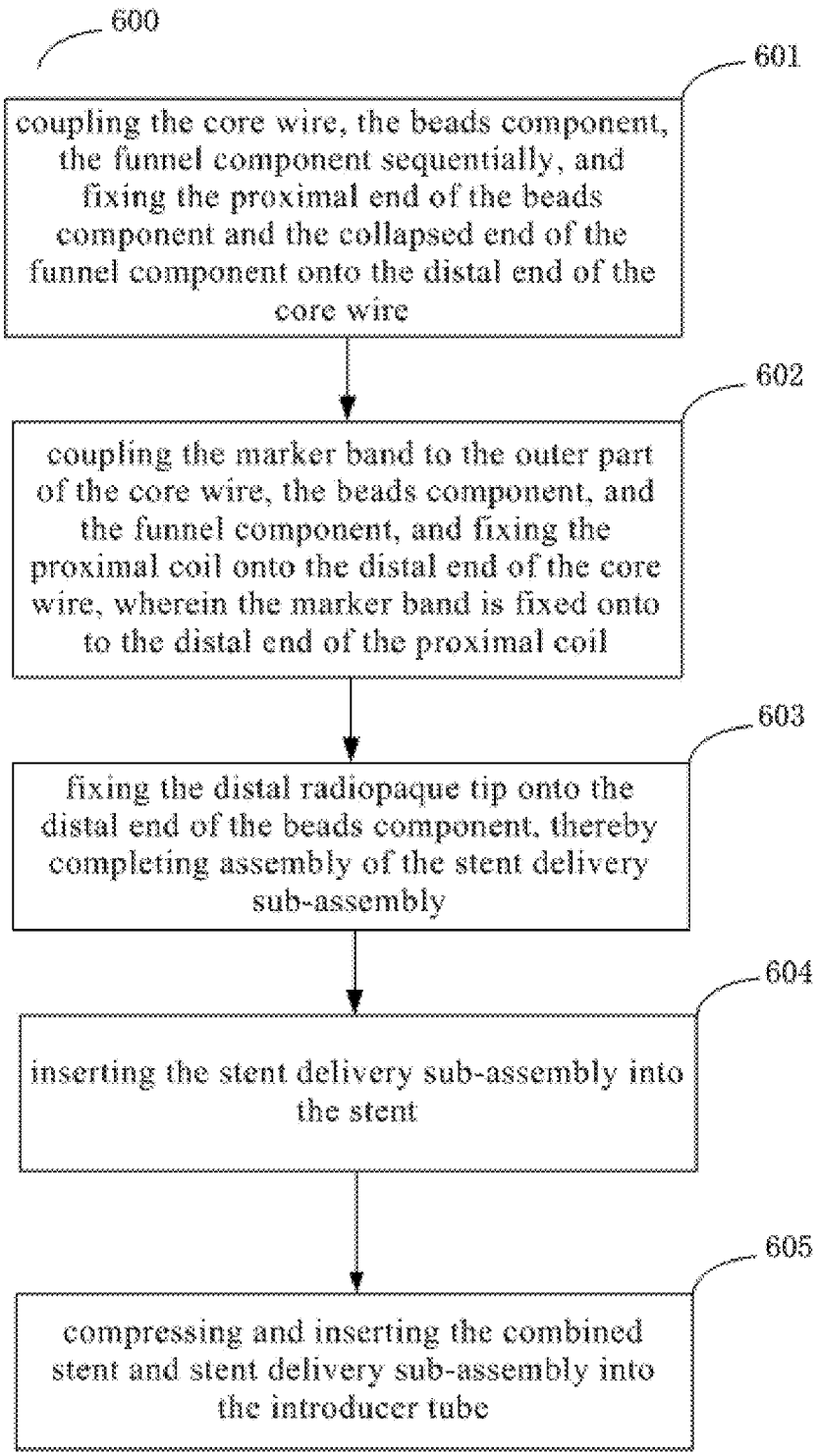
FIG. 6 is a process flow of an assembly method of a flow diversion device according to an embodiment of the present application.

FIG. 6 illustrates a process flow of an assembly method 600 for a flow diversion device according to an embodiment of the present application. The method includes steps 601-605.

At step 601, coupling the core wire, the beads component, the funnel component sequentially from inside to outside, and fixing the proximal end of the beads component and the collapsed end of the funnel component onto the distal end of the core wire.

At step 602, coupling the marker band to the outer part of the core wire, the beads component, and the funnel component, and fixing the proximal coil onto the distal end of the core wire, wherein the marker band is fixed onto to the distal end of the proximal coil.

At step 603, fixing the distal radiopaque tip onto the distal end of the beads component, thereby completing assembly of the stent delivery sub-assembly.

At step 604, inserting the stent delivery sub-assembly into the stent.

At step 605, compressing and inserting the combined stent and stent delivery sub-assembly into the introducer tube.

In one embodiment, in steps 601 and 602, heat-curing epoxy adhesives may be applied at key points to glue various components together. In another embodiment, in step 603, ultraviolet (UV)-curing adhesives may be applied at corresponding key points.

In one embodiment, the assembly method 600 also includes coupling the heat-shrink tube to the proximal end of the core wire. In another embodiment, the assembly method 600 also includes sterilizing the assembled flow diversion device.

The stent delivery system, the corresponding flow diversion device, and the assembly method of the flow diversion device provided by the present application have been described above in connection with the accompanied figures. The devices described above may be utilized for treatment of aneurysms and may facilitate easy deployment and retrieval of the stent. Using the devices described above may reduce risks in interventional surgeries as well as rejection rate of expensive medical equipments, thereby improving the success rate and economy of interventional treatment for aneurysms. Moreover, the devices described above are suitable for stents of various designs and materials and do not rely on any particular design and manufacturing process of the stent, thereby also improving versatility of the devices.

The previous description of the disclosed embodiments is provided to enable any person skilled in the art to make or use the present application. Various modifications to these embodiments will be readily apparent to those skilled in the art, and the generic principles defined herein may be applied to other embodiments without departing from the spirit or scope of the invention. Thus, the present application is not intended to be limited to the embodiments shown herein but is to be accorded the widest scope consistent with the principles and novel features disclosed herein.

Furthermore, although the operation of a method according to the present application is illustrated with reference to the accompanying drawings in a specific sequence, the present application may be practiced using process flows that differ from that illustrated. Additionally, it should be noted that not all steps are required in every embodiment. In other words, one or more of the steps may be omitted or replaced, without departing from the spirit and scope of the invention. In certain embodiments, steps may be performed in different order, in parallel with one another, or omitted entirely, and/or certain additional steps may be performed without departing from the scope of the present application.

In the claims, the word "comprising" does not exclude other elements or steps, and the indefinite article "a" or "an" does not exclude a plurality.

What is claimed is:

1. A stent delivery system comprising:
   a radiopaque tip located at a distal end of the stent delivery system;
   a beads component comprising at least one expandable part;
   a funnel component comprising a distal flare structure and a proximal collapsed end, wherein a cross-section of the flare structure gradually increases from its minimum diameter to its maximum diameter along the proximal-to-distal direction; a core wire located at a proximal end of the stent delivery system; and
   wherein a distal end of the beads component is fixed on the radiopaque tip and a proximal end of the beads component is fixed on the core wire;
   wherein the funnel component is coupled with the beads component and the core wire, and is fixed on the core wire through the collapsed end,
   wherein the stent delivery system is configured to deliver vascular stents to a target position during treatment of aneurysms;
   wherein a proximal coil is coupled to the outermost part of the distal end of the core wire, and the proximal coil is fixed on the core wire; and
   wherein a marker band is also coupled to the outermost part of the distal end of the core wire, the marker band being located at the distal end of the proximal coil and being fixed on the proximal coil.

2. The stent delivery system of claim 1, wherein the beads component comprises a plurality of expandable parts and a plurality of non-expandable parts arranged alternatively in the axial direction.

3. The stent delivery system of claim 2, wherein the plurality of expandable parts are in at least one of a bipyramid shape, a spherical shape, a flat-spherical shape, or a long-spherical shape.

4. The stent delivery system of claim 2, wherein the beads component and the funnel component are made of super-elastic materials, shape memory materials, or piezoelectric materials.

5. The stent delivery system of claim 2, wherein the beads component and the funnel component are made through a fine wire braiding technique.

6. The stent delivery system of claim 5, wherein the beads component is braided with six to sixty-four fine wires, and the funnel component is braided with four to twenty-four fine wires.

7. The stent delivery system of claim 5, wherein the braided density of the beads component is between 20 PPI and 250 PPI.

8. The stent delivery system of claim 1, wherein the beads component comprises a plurality of expandable parts arranged continuously along the axial direction and two non-expandable parts located at the two ends.

9. The stent delivery system of claim 8, wherein the plurality of expandable parts are in at least one of a bipyramid shape, a spherical shape, a flat-spherical shape, or a long-spherical shape.

10. The stent delivery system of claim 8, wherein the beads component and the funnel component are made of super-elastic materials, shape memory materials, or piezoelectric materials.

11. The stent delivery system of claim 8, wherein the beads component and the funnel component are made through a fine wire braiding technique.

12. The stent delivery system of claim 1, wherein the beads component comprises a coil, wherein the coil comprises at least two portions in different diameters.

13. The stent delivery system of claim 1, wherein a heat-shrink tube is coupled to the proximal end of the core wire.

14. The stent delivery system of claim 1, wherein the radiopaque tip, the beads component, the funnel component, the core wire, the marker band, and the proximal coil are fixed through gluing.

15. The stent delivery system of claim 14, wherein the radiopaque tip and the beads component are glued by ultraviolet (UV)-curing adhesives.

16. The stent delivery system of claim 14, wherein the beads component, the funnel component, the core wire, the marker band, and the proximal coil are glued by heat-curing epoxy adhesives.

17. The stent delivery system of claim 1, wherein a covering part is provided on the radiopaque tip to confine all open ends at the distal end of the beads component within the covering part.

18. A flow diversion device, comprising a stent, a stent delivery system, and an introducer tube, wherein the stent and the stent delivery system are confined within a lumen of the introducer tube under an initial state, and wherein, the stent delivery system comprises: a radiopaque tip located at a distal end of the stent delivery system; a beads component comprising at least one expandable part; a funnel component comprising a distal flare structure and a proximal collapsed end, wherein a cross-section of the flare structure gradually increases from its minimum diameter to its maximum diameter along the proximal-to-distal direction; and a core wire located at a proximal end of the stent delivery system; and wherein a distal end of the beads component is fixed on the radiopaque tip and a proximal end of the beads component is fixed on the core wire; and wherein the funnel component is coupled with the beads component and the core wire, and is fixed on the core wire through the collapsed end; and wherein, under the initial state, the stent is located outside the beads component, and the flare structure of the funnel component covers at least a proximal part of the stent.

19. The flow diversion device of claim 18, wherein the number and maximum diameter of the at least one expandable part are determined respectively according to the length and diameter of the stent.

20. The flow diversion device of claim 18, wherein compared with the length and the maximum diameter under a fully deployed state, the length is shorter and the maximum diameter is smaller under the initial state for each expandable part.

21. The flow diversion device of claim 18, wherein under a fully deployed state, the maximum diameter of the flare structure of the funnel component is larger than the maximum diameter at the proximal end of the stent.

22. The flow diversion device of claim 18, wherein a proximal coil is coupled to the outermost part of the distal end of the core wire, and the proximal coil is fixed on the core wire.

23. The flow diversion device of claim 22, wherein a marker band is also coupled to the outermost part of the distal end of the core wire, the marker band being located at the distal end of the proximal coil and being fixed on the proximal coil.

24. The flow diversion device of claim 18, wherein a heat-shrink tube is coupled to the proximal end of the core wire.

* * * * *